United States Patent
Gaudin et al.

(10) Patent No.: US 9,597,322 B2
(45) Date of Patent: Mar. 21, 2017

(54) OTAMIXABAN FOR USE IN THE TREATMENT OF NON-ST ELEVATION ACUTE CORONARY SYNDROME IN PATIENTS PLANNED TO UNDERGO CORONARY ARTERY BYPASS GRAFTING

(71) Applicant: SANOFI, Paris (FR)

(72) Inventors: Christophe Gaudin, Paris (FR); Angèle Moryusef, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/424,529

(22) PCT Filed: Aug. 29, 2013

(86) PCT No.: PCT/EP2013/067919
§ 371 (c)(1),
(2) Date: Feb. 27, 2015

(87) PCT Pub. No.: WO2014/033221
PCT Pub. Date: Mar. 6, 2014

(65) Prior Publication Data
US 2015/0202190 A1 Jul. 23, 2015

(30) Foreign Application Priority Data
Aug. 31, 2012 (EP) .................................... 12306041

(51) Int. Cl.
*A61K 31/4418* (2006.01)
*A61K 31/4409* (2006.01)

(52) U.S. Cl.
CPC ...... *A61K 31/4418* (2013.01); *A61K 31/4409* (2013.01)

(58) Field of Classification Search
None
See application file for complete search history.

(56) References Cited

FOREIGN PATENT DOCUMENTS

| WO | 9724118 A1 | 7/1997 |
|---|---|---|
| WO | 2011012527 A1 | 2/2011 |

OTHER PUBLICATIONS

Bassand, Jean-Perre "Guidelines for the diagnosis and treatment of non-ST-segment elevation acute coronary syndromes" European Heart Journal (2007) 28, 1598-1660.
Cohen, Marc "Randomized, Double-Blind, Dose-Ranging Study of Otamixaban, a Novel, Parenteral, Short-Acting Direct Factor Xa Inhibitor, in Percutaneous Coronary Intervention: The SEPIA-PCI Trial" Circulation 2007;115:2642-2651 (May 14, 2007).
Cole, P. "Otamixaban Coagulation Factor Xa Inhibitor Treatment of Acute Coronary Syndrome" Drugs of the Future 2010, 35(9): 719-727.
Gabriel, Philippe "Design and rationale of the Treatment of Acute Coronary Syndromes with Otamixaban trial: A double-blind triple-dummy 2-stage randomized trial comparing otamixaban to unfractionated heparin and eptifibatide in non-ST-segment elevation acute coronary syndromes with a planned early invasive strategy" Am Hear J 2012; 164:817-824 (Dec. 2012).
Guertin, Kevin The Discovery of the Factor Xa Inhibitor Otamixaban: From Lead Identification to Current Medicinal Chemistry, 2007, 14, 2471-2481.
Hinder, Markus "Direct and rapid inhibition of factor Xa by otamixaban: A pharmacokinetic and pharmacodynamic investigation in patients with coronary artery disease" Clinical Pharmacology & Therapeutics, 691-702 (Dec. 2006).
Thygesen, Kristian "Universal definition of myocardial infarction" European Heart Journal (2007) 28, 2525-2538.
Thygesen, Kristian "Universal definition of myocardial infarction" JACC vol. 50, No. 22, 2007 p. 2173-2195 (Nov. 27, 2007).

*Primary Examiner* — Samantha Shterengarts
(74) *Attorney, Agent, or Firm* — McDonnell Boehnen Hulbert & Berghoff

(57) ABSTRACT

The invention relates to otamixaban or a pharmaceutically acceptable salt thereof for use in the treatment of non-ST elevation acute coronary syndrome in patients planned to undergo coronary artery bypass grafting.

13 Claims, No Drawings

OTAMIXABAN FOR USE IN THE TREATMENT OF NON-ST ELEVATION ACUTE CORONARY SYNDROME IN PATIENTS PLANNED TO UNDERGO CORONARY ARTERY BYPASS GRAFTING

This application is a national stage application under 35 U.S.C. §371 of International Application No. PCT/EP2013/067919, filed Aug. 29, 2013, which claims the priority of European Application No. 12306041.0 filed on Aug. 31, 2012.

FIELD OF THE INVENTION

The present invention relates to patients suffering from non-ST elevation acute coronary syndrome treated with otamixaban in patients planned to undergo coronary artery bypass grafting (CABG).

BACKGROUND OF THE INVENTION (2R,3R)-2-(3-Carbamimidoyl-benzyl)-3-[4-(1-oxy-pyridin-4-yl) benzoylamino]-butyric acid methyl ester, (CAS number 193153-04-7) has the International Nonproprietary Name Otamixaban and shows the structure illustrated in Formula I:

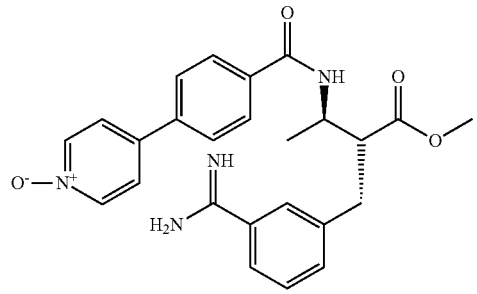

Formula I (2R,3R)-2-(3-Carbamimidoyl-benzyl)-3-[4-(1-oxy-pyridin-4-yl) benzoylamino]-butyric acid methyl ester (Otamixaban, Formula I) use in the preparation of a medicament for treating a patient suffering from, or subject to, conditions which can be ameliorated by the administration of an inhibitor of Factor Xa has been disclosed in WO97/24118.

Factor Xa is the penultimate enzyme in the coagulation cascade. Factor Xa (fXa) is a critical serine protease situated at the confluence of the intrinsic and extrinsic pathways of the blood coagulation cascade. FXa catalyses the conversion of prothrombin to thrombin via the prothrombinase complex. Its singular role in thrombin generation, coupled with its potentiating effects on clot formation render it an attractive target for therapeutic intervention.

Both free factor Xa and factor Xa assembled in the prothrombinase complex (Factor Xa, Factor Va, calcium and phospholipid) are inhibited by Otamixaban. Factor Xa inhibition is obtained by direct complex formation between the inhibitor and the enzyme and is therefore independent of the plasma co-factor antithrombin III. Effective factor Xa inhibition is achieved by administering the compound either by continuous intravenous infusion, bolus intravenous administration or any other parenteral route such that it achieves the desired effect of preventing the factor Xa induced formation of thrombin from prothrombin. In vivo experiments have demonstrated that Otamixaban is highly efficacious in rodent, canine and porcine models of thrombosis. In addition, recent clinical findings indicate that Otamixaban is efficacious, safe and well tolerated in humans and therefore has considerable potential for the treatment of acute coronary syndrome (K. R. Guertin and Yong-Mi Choi; 2007; Current Medicinal Chemistry, Vol. 14, No. 23; p. 2471-2481). Clinical findings in a dose-ranging clinical trial indicate that Otamixaban reduced prothrombin fragments 1+2 significantly more than unfractionated heparin at the highest dose regimen (Cohen et al., Circulation, Vol. 115, No. 20, May 2007, pages 2642-2651), but said clinical findings do not show data in comparison of age or renal impairment. Further clinical trials demonstrated that Otamixaban induces dose-dependent, rapid direct factor Xa inhibition in patients with stable coronary artery disease who are taking their usual comedication, some of whom have mild renal impairment (Hinder et al., Clinical Pharmacology and Therapeutics, Vol. 80, No. 6, 2006, pages 691-702).

Acute coronary syndromes (ACS) are characterised by an imbalance between myocardial oxygen supply and demand. The most common cause is the reduced myocardial perfusion that results from coronary artery narrowing caused by a thrombus that has developed on a disrupted atherosclerotic plaque. Within the diagnosis of ACS two major subtypes can be distinguished that are non-ST elevation acute coronary syndrome (NSTE-ACS) and ST-elevation myocardial infarction (STE-MI). NSTE-ACS corresponds to a partial thrombotic occlusion of a coronary vessel with more or less pronounced ischemia. The main aim of treatment for these conditions is to prevent a sudden total occlusion of the arteries. STE-MI is characterised by a sudden total thrombotic occlusion of a coronary vessel resulting in ischemia of the heart. It needs to be treated urgently, within the initial 6-12 hours, and preferably 2 hours following the diagnosis. The goal is to restore patency (blood flow) of the occluded vessel. This can be performed by angioplasty, percutaneous coronary intervention or coronary artery bypass grafting (CABG). CABG is an open heart surgery in which a prosthesis or a section of a vein is grafted from the aorta onto one of the coronary arteries, bypassing a narrowing or blockage in the coronary artery. The operation is performed in coronary artery disease to improve the blood supply to the heart muscle and to relieve anginal pain. Coronary arteriography pinpoints the areas of obstruction before surgery. Under general anesthesia and with the use of a cardiopulmonary bypass machine, one end of a 15- to 20-cm prosthesis or a segment of saphenous vein from the patient's leg is grafted to the ascending aorta. The other end is sutured to the clogged coronary artery at a point distal to the stoppage. The internal mammary artery may also be used as graft tissue. Usually double or triple grafts are done for multiple areas of blockage. After surgery, close observation in an intensive care unit is essential to ensure adequate ventilation and cardiac output.

Risk scores have been developed that regroup markers of the acute thrombotic process and other markers to identify patients with high-risk for total occlusion of vessels; in the following high-risk patients for coronary artery disease or peripheral arterial disease. In addition to the estimation of the risk, the assessment of the cardiac biomarker of necrosis, especially the cardiac troponins, are performed in order to select the treatment strategy of choice. It has been demonstrated during the last years that patients with moderate-to-high risk patients benefit from an early invasive strategy, where patients are brought early to a catheter lab (by the next day, or two) for angiography followed by a percutaneous coronary intervention (PCI) or a CABG. In recent US treatment guidelines for high-risk patients an invasive strategy is recommended for moderate-to-high risk patients while for lower risk patients a conservative strategy is preferred. However, timely access to invasive treatment is often more important for the decision than risk assessment.

In all high-risk patients (with invasive or conservative strategy) a standard medical therapy is indicated including aspirin, clopidogrel and anticoagulant therapy.

The primary discussions in medical literature today is focused on the moderate-to-high-risk patients, who are scheduled to undergo an early (≤48-72 h) diagnostic catheterization and coronary intervention. Aspirin, clopidogrel, GP IIb/IIIa inhibitors (including eptifibatide and abciximab), unfractionated heparin, bivalirudin, enoxaparin, fondaparinux are all recommended in the most recent guidelines indicating their recognition as standard of care for patients with moderate-to-high-risk.

Use of such a multi-tiered combination pharmacologic approach, however, has not been formally investigated and may result in increased risk of bleeding complications, greater complexity of treatment and increased costs. Further the presently used combination therapy of heparin and GP IIb/IIIa inhibitor is efficacious but causes bleeding in high-risk patients receiving dual oral antiplatelet therapy with aspirin and clopidogrel. Thus, the optimal anti-thrombotic regimen for moderate-to-high-risk patients remains to be found.

It is an object of the present invention to find a medical treatment, which does not have the disadvantages mentioned and provides a reduction of bleeding rates in high-risk patients suffering from non-ST elevation acute coronary syndrome and planned to undergo coronary artery bypass grafting.

It has now unexpectedly been found that Otamixaban offers improved management of high-risk patients suffering from non-ST elevation acute coronary syndrome. If said patients are already being treated by administration of Otamixaban and are planned to undergo coronary artery bypass grafting (CABG), administration of Otamixaban to said patients will be discontinued at least 3 hours particularly 3 to 6 hours more particularly 6 hours or more prior to said coronary artery bypass grafting (CABG). Unexpectedly, said high-risk patents show a reduced risk of bleeding.

SUMMARY OF THE PRESENT INVENTION

The present invention provides (2R,3R)-2-(3-carbamimidoyl-benzyl)-3-[4-(1-oxy-pyridin-4-yl)benzoylamino]-butyric acid methyl ester or a pharmaceutically acceptable salt thereof for use in the treatment of non-ST elevation acute coronary syndrome in patients planned to undergo coronary artery bypass grafting, wherein the treatment of the patient comprises the steps of:
  (a) administration of (2R,3R)-2-(3-carbamimidoyl-benzyl)-3-[4-(1-oxy-pyridin-4-yl)benzoylamino]-butyric acid methyl ester or a pharmaceutically acceptable salt thereof, and
  (b) stopping the administration of (2R,3R)-2-(3-carbamimidoyl-benzyl)-3-[4-(1-oxy-pyridin-4-yl)benzoylamino]-butyric acid methyl ester or a pharmaceutically acceptable salt thereof prior to performing coronary artery bypass grafting.

DETAILED DESCRIPTION OF THE INVENTION

A first aspect of the invention is (2R,3R)-2-(3-carbamimidoyl-benzyl)-3-[4-(1-oxy-pyridin-4-yl)benzoylamino]-butyric acid methyl ester or a pharmaceutically acceptable salt thereof for use in the treatment of non-ST elevation acute coronary syndrome in patients planned to undergo coronary artery bypass grafting, wherein the treatment of the patient comprises the steps of
  (a) administration of (2R,3R)-2-(3-carbamimidoyl-benzyl)-3-[4-(1-oxy-pyridin-4-yl)benzoylamino]-butyric acid methyl ester or a pharmaceutically acceptable salt thereof, and
  (b) stopping the administration of (2R,3R)-2-(3-carbamimidoyl-benzyl)-3-[4-(1-oxy-pyridin-4-yl)benzoylamino]-butyric acid methyl ester or a pharmaceutically acceptable salt thereof prior to performing coronary artery bypass grafting.

Terms used herein have the meanings defined in this specification.

"Angioplasty" refers to a procedure used to open blocked or narrowed coronary (heart) arteries. The procedure improves blood flow to the heart muscle.

"Atherectomy" refers to a minimally invasive surgical method of removing, mainly plaque from a large blood vessel within the body. Today, it is generally used to effectively treat peripheral arterial disease of the lower extremities.

"Atherosclerosis" refers to a disease in which plaque builds up inside the arteries.

"Coronary artery bypass grafting" or "CABG" is a type of surgery that improves blood flow to the heart. It's used for people who have severe coronary artery disease. CABG is one treatment for coronary artery disease. During CABG, prosthesis, healthy artery or a section of a vein is grafted from the aorta onto one of the coronary arteries, bypassing a narrowing or blockage in the coronary artery. The grafted artery, prosthesis or vein bypasses the blocked portion of the coronary artery. Usually double or triple grafts are done for multiple areas of blockage. This creates a new passage, and oxygen-rich blood is routed around the blockage.

"CABG-related bleeding" will be classified as major according to the following definition (as per the TIMI classification):
  Fatal bleeding (i.e. bleeding that directly results in death),
  Perioperative intracranial bleeding,
  Reoperation following closure of the sternotomy incision for the purpose of controlling bleeding,
  Transfusion of ≥5 units of whole blood or packed red blood cells within a 48 hour period. Cell saver transfusion will not be counted in calculations of blood products,
  Chest tube output >2 L within a 24 hour period.
If a CABG-related bleeding is not adjudicated as a CABG major bleeding it will be classified as not a bleeding event, ie bleeding related to the fact that this is surgery "Coronary artery disease" refers to a condition in which plaque builds up inside the coronary arteries. The build up of plaque occurs over many years. Over time, plaque hardens and narrows the coronary arteries. This limits the flow of oxygen-rich blood to the heart muscle. If the flow of oxygen-rich blood to the heart muscle is reduced or blocked, angina or heart attack may occur.

"i. v." refers to intra venous injection.

"non-ST elevation myocardial infarction" and "unstable angina" refer to the definition of non-ST segment elevation acute coronary syndromes based on ACC/AHA, ESC Guidelines for the diagnosis and treatment of non-ST segment elevation acute coronary syndromes; Eur Heart J, 2007, 28(13): 1598-1660; J Am Coll Cardiol, 2007; 50:2173-2195; Eur Heart J, 2007, 28: 2525-2538.

"Otamixaban" is the international nonproprietary name for (2R,3R)-2-(3-carbamimidoyl-benzyl)-3-[4-(1-oxy-pyridin-4-yl)benzoylamino]-butyric acid methyl ester.

"Percutaneous coronary intervention" or "PCI" refers to any technique capable of relieving coronary narrowing, including but not limited to balloon angioplasty, rotational atherectomy, directional atherectomy, extraction atherectomy, laser angioplasty, and implantation of intracoronary stents and other catheter devices for treating plaque build up inside arteries.

"Peripheral arterial disease" refers to a narrowing of the blood vessels outside of the heart. This happens when plaque, a substance made up of fat and cholesterol, builds up on the walls of the arteries that supply blood to the arms, pelvis and legs. The plaque causes the arteries to narrow or become blocked. This can reduce or stop blood flow, usually to the legs, causing them to hurt or feel numb. If severe enough, blocked blood flow can cause tissue death. If this condition is left untreated, a foot or leg may need to be amputated.

"Pharmaceutically acceptable salt" is any non-toxic inorganic acid salt of the base compound (2R,3R)-2-(3-Carbamimidoyl-benzyl)-3-[4-(1-oxy-pyridin-4-yl) benzoylamino]-butyric acid methyl ester. Illustrative inorganic acids which form suitable salts include mineral acids, such as hydrochloric acid, hydrobromic acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. Preferably, the acid addition salt is derived from a mineral acid, with hydrochloric acid being preferred.

"Plaque" is made up of fat, cholesterol, calcium, and other substances found in the blood. Over time, plaque hardens and narrows the arteries. This limits the flow of oxygen-rich blood to the organs and other parts of the body.

"Restenosis" refers to reoccurrence of stenosis, which is a narrowing of a blood vessel, leading to restricted blood flow. Restenosis usually pertains to an artery or other large blood vessels that has become narrowed, received treatment to clear the blockage and subsequently become renarrowed. This is usually restenosis of an artery, or other blood vessel, or possibly a vessel within an organ.

"TIMI" is the abbreviation for the "Thrombolysis in Myocardial Infarction" and refers to the classification of bleeding.

"Therapeutically effective amount" refers an amount of the compound, which is effective in treating the named disorder or condition.

"Treat" or "treating" refers to any treatment, including, but not limited to, alleviating symptoms, eliminating the causation of the symptoms either on a temporary or permanent basis, or preventing or slowing the appearance of symptoms and progression of the named disorder or condition.

The synthesis of (2R,3R)-2-(3-carbamimidoyl-benzyl)-3-[4-(1-oxy-pyridin-4-yl)benzoylamino]-butyric acid methyl ester has been disclosed, and is accomplished by methods that are well known to those skilled in the art. For example International Application WO97/24118 discloses methods of synthesis.

In a further embodiment, said administration of (2R,3R)-2-(3-carbamimidoyl-benzyl)-3-[4-(1-oxy-pyridin-4-yl)benzoylamino]-butyric acid methyl ester or a pharmaceutically acceptable salt thereof in step (b) is stopped at least 3 hours, particularly between 3 hours and 6 hours prior, more particularly in a timeframe equal to or more than 6 hours prior to performing coronary artery bypass grafting In a further embodiment, said administration of (2R,3R)-2-(3-carbamimidoyl-benzyl)-3-[4-(1-oxy-pyridin-4-yl)benzoylamino]-butyric acid methyl ester or a pharmaceutically acceptable salt thereof is done at least two hours, particularly between two and seventy-two hours.

The patient to be treated by (2R,3R)-2-(3-carbamimidoyl-benzyl)-3-[4-(1-oxy-pyridin-4-yl)benzoylamino]-butyric acid methyl ester or a pharmaceutically acceptable salt thereof for may be an adult subject. The subject may have an age of at least 18 years or may have an age of 18 to 80 years, of 65 to 75 years, or 40 to 80 years, or 50 to 60 years. The subject may also be defined as a patient having an age lower than 65 years, between 65 to 75 years and greater than 75 years.

The patient to be treated by (2R,3R)-2-(3-carbamimidoyl-benzyl)-3-[4-(1-oxy-pyridin-4-yl)benzoylamino]-butyric acid methyl ester or a pharmaceutically acceptable salt thereof according to the present invention may suffer from non ST elevation acute coronary syndrome (non ST Elevation ACS) which comprises unstable angina and non ST elevation myocardial infarction (non STEMI).

Thus, in a further embodiment, patient to be treated by (2R,3R)-2-(3-carbamimidoyl-benzyl)-3-[4-(1-oxy-pyridin-4-yl)benzoylamino]-butyric acid methyl ester or a pharmaceutically acceptable salt thereof according to the present invention may suffer from non ST elevation acute coronary syndrome, more particularly unstable angina and non ST elevation myocardial infarction.

In a further embodiment the invention relates to (2R,3R)-2-(3-carbamimidoyl-benzyl)-3-[4-(1-oxy-pyridin-4-yl)benzoylamino]-butyric acid methyl ester or a pharmaceutically acceptable salt thereof for use in the treatment acute coronary syndrome particularly non ST elevation acute coronary syndrome, more particularly unstable angina and non ST elevation myocardial infarction.

In a further embodiment the invention relates to (2R,3R)-2-(3-carbamimidoyl-benzyl)-3-[4-(1-oxy-pyridin-4-yl)benzoylamino]-butyric acid methyl ester or a pharmaceutically acceptable salt thereof for use in the treatment of Non ST Elevation ACS wherein administration of (2R,3R)-2-(3-carbamimidoyl-benzyl)-3-[4-(1-oxy-pyridin-4-yl)benzoylamino]-butyric acid methyl ester or a pharmaceutically acceptable salt thereof is stopped between 3 hours and 6 hours before performing coronary artery bypass grafting. In particular administration is stopped a timeframe equal to or more than 6 hours prior to performing coronary artery bypass grafting.

In a further embodiment, said pharmaceutically acceptable salt is an hydrochloride salt.

The relative amounts of otamixaban and acid in the salts may vary and depends, for example, on the particular acid selected and the methods employed in preparing the salts. Preferably, the salts of the present invention comprise about one equivalent of acid for about each equivalent of otamixaban.

The acid addition salts of otamixaban may be prepared by dissolving the free base in aqueous or aqueous-alcohol solution or other suitable solvents containing the appropriate acid or to which the appropriate acid is added, and isolating the salt by evaporating the solution, or by reacting the free base and acid in an organic solvent, in which case the salt may separate directly and/or may be obtained by concentration of the solution.

In general in the adult population, suitable infusion doses of (2R,3R)-2-(3-carbamimidoyl-benzyl)-3-[4-(1-oxy-pyridin-4-yl)benzoylamino]-butyric acid methyl ester may range from 0.07 mg/Kg body weight/h to 0.175 mg/Kg body weight/h, particularly 0.10 mg/Kg body weight/h to 0.14 mg/Kg body weight/h more particularly 0.07, 0.1, 0.14 or 0.175 mg/Kg body weight/h. Said dosage form may also be delivered in an intravenous bolus dose. In general in the adult population, suitable bolus doses of (2R,3R)-2-(3-carbamimidoyl-benzyl)-3-[4-(1-oxy-pyridin-4-yl)benzoylamino]-butyric acid methyl ester is 0.08 mg/Kg body weight. Also a suitable dose balancing patient safety and efficacy will be a dose close to 0.1 mg/kg body weight/h after i.v. bolus of approximately 0.08 mg/kg body weight or a dose close to 0.14 mg/kg body weight/h after i.v. bolus of approximately 0.08 mg/kg body weight Methods of administrating the pharmaceutical composition according to the invention parenterally are well known in the art. For example, the injectable aqueous pharmaceutical composition may be delivered intravenously in a specific dosage form. Said dosage form may be delivered in an intravenous infusion dose.

Sterile injectable solutions may be prepared by incorporating otamixaban in the required amounts, in the appropriate solvent, with various of the other ingredients enumerated herein, as required, followed by filtered sterilization. Generally, dispersions may be prepared by incorporating the sterilized active ingredient into a sterile vehicle which contains the dispersion medium and any other required ingredients. In the case of sterile powders for the preparation of sterile injectable solutions, the preferred methods of preparation may include vacuum drying and the freeze drying technique which may yield a powder of the active ingredient, plus any additional desired ingredient from the previously sterile-filtered solution thereof.

Liquid compositions may also contain other components routinely utilized in formulating pharmaceutical compositions. One example of such components is lecithin. Its use in compositions of the invention as an emulsifying agent may range from about 0.05 to about 1% by weight, and all combinations and subcombinations of ranges and specific amounts therein. More preferably, emulsifying agents may be employed in an amount of from about 0.1 to about 0.5% by weight. Other examples of components that may be used are antimicrobial preservatives, such as benzoic acid or parabens; suspending agents, such as colloidal silicon dioxide; antioxidants; topical oral anesthetics; flavoring agents; and colorants.

The selection of such optional components and their level of use in the compositions of the invention is within the level of skill in the art and will be even better appreciated from the working examples provided hereinafter.

In general, water, a suitable oil, saline, aqueous dextrose (glucose), and related sugar solutions and glycols, such as propylene glycol or polyethylene glycols may be suitable carriers for parenteral solutions. Solutions for parenteral solutions may be prepared by dissolving Otamixaban in the carrier and, if necessary, adding buffering substances. Antioxidizing agents, such as sodium bisulfite, sodium sulfite, or ascorbic acid either alone or combined, may be suitable stabilizing agents. Citric acid and its salts and sodium EDTA may also be employed. Parenteral solutions may also contain preservatives, such as benzalkonium chloride, methyl- or propyl-paraben and chlorobutanol.

Useful pharmaceutical dosage-forms for administration of otamixaban can be illustrated as follows:

Suspensions

An aqueous suspension may be prepared for oral administration so that each 5 mL contains 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection may be prepared by stirring 1.5% by weight of active ingredient in 10% by volume propylene glycol and water. The solution may be sterilized by commonly used techniques.

The following non-limiting examples illustrate the inventors' preferred methods for preparing and using the pharmaceutical compositions of the present invention.

EXAMPLES

Example 1

Preparation of Compound (III)

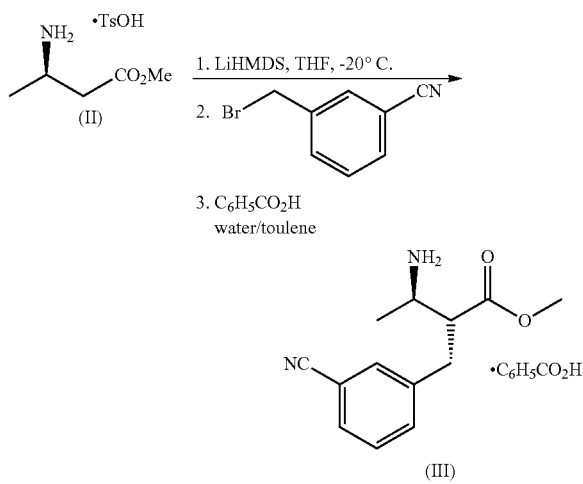

TsOH is p-Toluenesulfonic acid with the formula $CH_3C_6H_4SO_3H$. TsOH refers to the monohydrate. To a reactor were charged Compound (II) (100.0 g) and anhydrous tetrahydrofuran (THF) (320 g). The resulting suspension was cooled down to −20±3° C. and lithium hexamethyldisilazide (LiHMDS) (475.6 grams, 1.3 M solution in THF) was added over 55 minutes and stirred for 20 minutes at −20±3° C. A solution of α-bromo-m-tolunitrile in THF (65.1 g in 181 g of THF) was then charged into the reactor over 40 minutes while maintaining the temperature at −20±3° C. and stirred for another 30 minutes. Benzoic acid (126.6 grams) was charged as a solid to the reactor. Water (1000 g) was then added and mixture distilled at a 65±3° C. jacket temperature and 200-233 mbar vacuum. After distilling to a constant pot temperature of 57° C. and constant head temperature of 45° C., the distillation was stopped. Toluene (432 g) was added to the hot solution and stirred while cooling down to 10±2° C. The resulting suspension was then filtered and the filter cake washed with water (250 grams) and toluene (432 grams). Compound (III) was dried at 45-50° C. at ~350 mbar vacuum under a nitrogen stream for 24 hours until constant weight. The isolated solid weighed 76.0 grams (62.0% yield).

Example 2

Preparation of Compound (V)

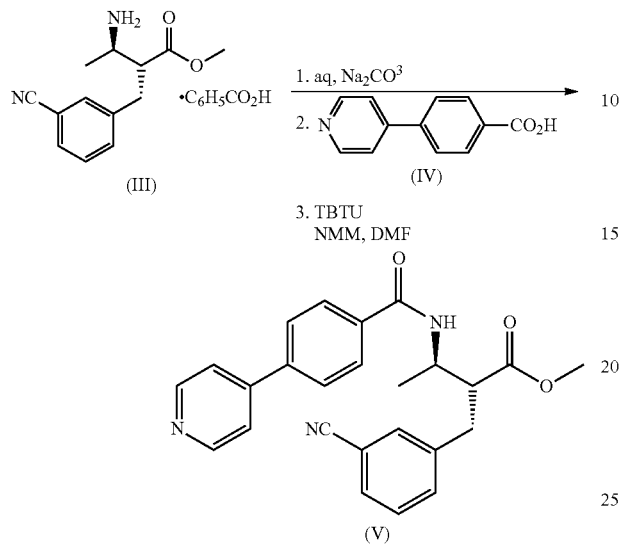

Compound (III) was partitioned between dichloromethane and aqueous sodium carbonate. The organic phase (containing the free base of (III)) was washed with additional aqueous sodium carbonate and was distilled under reduced pressure and solvent exchanged with dimethylformamide (DMF). This solution was assayed for wt/wt content of (III). To a suspension of (IV) (1.0 equivalent vs. (III)) in DMF were added 2 equivalents of 4-methylmorpholine and 1.1 equivalents of O-Benztriazol-1-yl-N,N,N',N'-tetramethyluronium tetrafluoroborate (TBTU). This mixture was stirred at ambient temperature until ester activation was complete (about 90 minutes). The DMF solution of Compound (III) (1 equivalent) was added and the resulting solution stirred overnight after which HPLC indicated that the reaction was complete. Water was added at 75° C. and the mixture was cooled to crystallize the product. The mixture was cooled to 5° C., filtered, and the filter cake was washed with water. The product was dried under reduced pressure at 70° C.

Example 3

Preparation of Compound (VI)

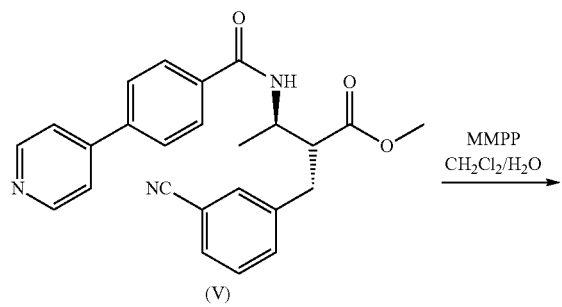

In a well-stirred reactor, 45 g of Compound (V) in 450 mL dichloromethane was reacted for at least 5 hours with 61 g of magnesium monoperoxyphthalate (66.4% based on available oxygen, 1.5 eq.) in 450 g of water until the reaction was complete. The phases were separated and the organic phase was washed successively with equal volumes of water, a 5% aqueous sodium bicarbonate solution, and water. The resulting solution was concentrated to an approximately 40 wt % solution and diluted with 180 g of methyl isobutyl ketone (MIBK). Further distillation to remove residual dichloromethane, seeding with appropriate crystals, and cooling gave the product as a crystalline solid. The crystals were filtered, rinsed with 30 g of MIBK, and dried at 50° C. under reduced pressure to give 41.8 g of Compound (VI) (89.3% yield).

Example 4

Preparation of Compound (I)

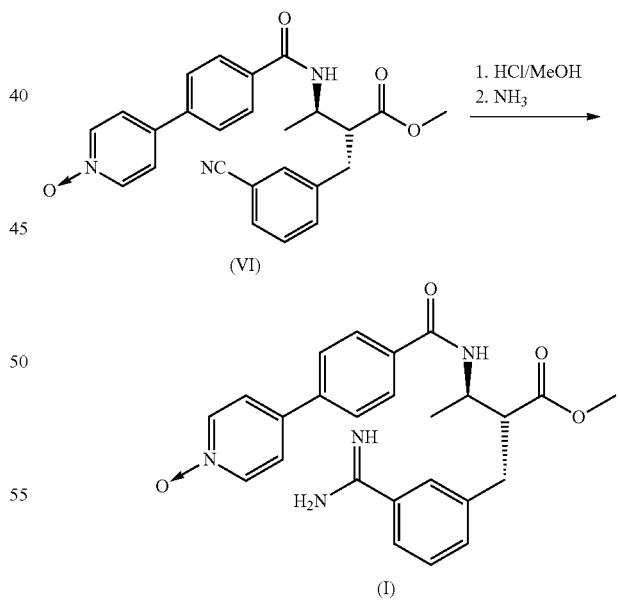

To a 200-mL jacketed reaction flask were charged Compound (VI) (50.0 g, 116 mmol) and methanol (50 mL). This mixture was cooled to −5° C. and sealed after establishing a partial vacuum (about 100 torr). Anhydrous HCl (52.2 g, 1.43 mol) was added while maintaining the reaction temperature at less than 0° C. The reaction was stirred at 0±1° C. under closed conditions. After 16 hours, the reaction was complete (less than 2 A % (VI) by HPLC). To the intermediate product solution was added anhydrous methanol (100 mL) while maintaining the temperature at less than 5° C. The solution was treated with $NH_3$ (27.7 g, 1.62 mol) keeping the temperature less than 0° C. Before allowing the mixture to warm to room temperature, a pH check was made of an aliquot dissolved in DI water (a pH of 8-10 indicates a sufficient charge of ammonia). The reaction was stirred at 20° C. overnight at which point the reaction was complete.

Example 5

The following results are based on a randomized, double-blind triple-dummy trial in patients with Unstable angina/Non ST segment Elevation Myocardial infarction scheduled to undergo an early invasive strategy (SEPIA ACS trial).

This was a multinational, randomized, double-blind, triple-dummy, dose-ranging study with 6 parallel groups. Patients were to be randomized (1:1:1:1:1:1) to 1 of 5 otamixaban dosage regimens (given as a 0.08 mg/kg bolus followed by an infusion of 0.035-0.175 mg/kg/hr) or unfractionated heparin plus eptifibatide. Otamixaban as the hydrochloride salt or unfractionated heparin was administered from randomization, until the end of the PCI, or if no PCI as clinically indicated, up to Day 4 or until hospital discharge, whichever came first. Eptifibatide was only given in the unfractionated heparin group and was given from the time of randomization until, if the patient underwent PCI, 18-24 hours post-PCI or until hospital discharge, whichever came first. If no PCI, was performed eptifibatide might be discontinued or could be given as long as clinically indicated (maximum of 72 hours). All patients were treated with aspirin and clopidogrel, as recommended in the American College of Cardiology/American Heart Association (ACC/AHA) and European Society of Cardiology (ESC) guidelines.

Among the patients under treatment with otamixaban, patients were discontinued the drug before coronary artery by pass surgery (CABG).

Table 1 presents in patients having a coronary artery by pass surgery (CABG), the incidence of CABG related bleeding (according to the TIMI classification), according to the delay between discontinuation of the otamixaban infusion and the start of the CABG:

TABLE 1

| Delay between otamixaban infusion discontinuation and CABG surgery start | Ota.: 0.035 [mg/Kg/h] (N = 11) | Ota.: 0.070 [mg/Kg/h] (N = 71) | Ota.: 0.105 [mg/Kg/h] (N = 79) | Ota.: 0.140 [mg/Kg/h] (N = 68) | Ota.: 0.175 [mg/Kg/h] (N = 66) | All (N = 295) |
|---|---|---|---|---|---|---|
| <3 h CABG related major TIMI bleeding | | | | | | |
| No | 1 (100%) | 0 | 0 | 1 (50.0%) | 0 | 2 (25.0%) |
| Yes | 0 | 1 (100%) | 1 (100%) | 1 (50.0%) | 3 (100%) | 6 (75.0%) |
| 3 h-6 h CABG related major TIMI bleeding | | | | | | |
| No | 2 (100%) | 3 (75.0%) | 3 (50.0%) | 1 (33.3%) | 0 | 9 (60.0%) |
| Yes | 0 | 1 (25.0%) | 3 (50.0%) | 2 (66.7%) | 0 | 6 (40.0%) |
| >6 h CABG related major TIMI bleeding | | | | | | |
| No | 8 (100%) | 61 (92.4%) | 65 (90.3%) | 57 (90.5%) | 55 (87.3%) | 246 (90.4%) |
| Yes | 0 | 5 (7.6%) | 7 (9.7%) | 6 (9.5%) | 8 (12.7%) | 26 (9.5%) |

<3 h means less than 3 hours between end of Ota treatment and CABG start
3 h-6 h means from 3 to 6 hours between end of Ota treatment and CABG start
>6 h means more than 6 hours between end of Ota treatment and CABG start
N means number of patients
Ota. means the compound Otamixaban and the used amount in the continuous infusion in mg/Kg/h

What is claimed is:

1. A method for treating non-ST elevation acute coronary syndrome in a patient planned to undergo coronary artery bypass grafting, the method comprising
   (a) administration of an effective amount of (2R,3R)-2-(3-carbamimidoyl-benzyl)-3-[4-(1-oxy-pyridin-4-yl) benzoylamino]-butyric acid methyl ester or a pharmaceutically acceptable salt thereof to the patient before the coronary artery bypass grafting, and then
   (b) stopping the administration of (2R,3R)-2-(3-carbamimidoyl-benzyl)-3-[4-(1-oxy-pyridin-4-yl) benzoylamino]-butyric acid methyl ester or the pharmaceutically acceptable salt thereof 3 or more and less than 6 hours prior to the coronary artery bypass grafting,
   wherein the administration of (2R,3R)-2-(3-carbamimidoyl-benzyl)-3-[4-(1-oxy-pyridin-4-yl) benzoylamino]-butyric acid methyl ester or the pharmaceutically acceptable salt thereof is in the form of an infusion dose in the range from 0.10 mg/Kg body weight/h to 0.14 mg/Kg body weight/h.

2. The method of claim 1, wherein the pharmaceutically acceptable salt is the hydrochloride salt.

3. The method of claim 1, wherein the non-ST elevation acute coronary syndrome is non-ST elevation myocardial infarction.

4. The method of claim 1, wherein the administration in step (b) is stopped at 6 hours prior to performing coronary artery bypass grafting.

5. The method of claim 1, wherein the administration of (2R,3R)-2-(3-carbamimidoyl-benzyl)-3-[4-(1-oxy-pyridin-4-yl) benzoylamino]-butyric acid methyl ester or a pharmaceutically acceptable salt thereof further includes a bolus dose of about 0.08 mg/Kg body weight.

6. The method of claim 5, wherein the administration of (2R,3R)-2-(3-carbamimidoyl-benzyl)-3-[4-(1-oxy-pyridin-4-yl) benzoylamino]-butyric acid methyl ester or the pharmaceutically acceptable salt thereof is in the form of an i.v. bolus dose of approximately 0.08 mg/kg body weight followed by an infusion dose of approximately 0.1 mg/kg body weight/h.

7. The method of claim 5, wherein the administration of (2R,3R)-2-(3-carbamimidoyl-benzyl)-3-[4-(1-oxy-pyridin-4-yl) benzoylamino]-butyric acid methyl ester or the pharmaceutically acceptable salt thereof is in the form of an i.v. bolus dose of approximately 0.08 mg/kg body weight followed by an infusion dose of approximately 0.14 mg/kg body weight/h.

8. The method of claim 1, wherein the patient has an age of at least 18 years.

9. The method of claim 5, wherein the administration of (2R,3R)-2-(3-carbamimidoyl-benzyl)-3-[4-(1-oxy-pyridin-4-yl) benzoylamino]-butyric acid methyl ester or the pharmaceutically acceptable salt thereof is in the form of an i.v. bolus dose of approximately 0.08 mg/kg body weight followed by an infusion dose of approximately 0.1 mg/kg body weight/h.

10. The method of claim 5, wherein the administration of (2R,3R)-2-(3-carbamimidoyl-benzyl)-3-[4-(1-oxy-pyridin-4-yl) benzoylamino]-butyric acid methyl ester or the pharmaceutically acceptable salt thereof is in the form of i.v. bolus dose of approximately 0.08 mg/kg body weight followed by an infusion dose of approximately 0.14 mg/kg body weight/h.

11. A method for reducing the incidence of coronary artery bypass grafting related bleeding in a patient following coronary artery bypass grafting, the method comprising
(a) administration to the patient of an effective amount of (2R,3R)-2-(3-carbamimidoyl-benzyl)-3-[4-(1-oxy-pyridin-4-yl) benzoylamino]-butyric acid methyl ester or a pharmaceutically acceptable salt thereof; and
(b) stopping the administration of the (2R,3R)-2-(3-carbamimidoyl-benzyl)-3-[4-(1-oxy-pyridin-4-yl) benzoylamino]-butyric acid methyl ester or the pharmaceutically acceptable salt thereof at least 3 hours prior to the coronary artery bypass grafting.

12. The method of claim 11, wherein the administration of (2R,3R)-2-(3-carbamimidoyl-benzyl)-3-[4-(1-oxy-pyridin-4-yl) benzoylamino]-butyric acid methyl ester or the pharmaceutically acceptable salt thereof is stopped at least three hours but less than 6 hours before the coronary artery bypass grafting.

13. The method of claim 11, wherein the administration of (2R,3R)-2-(3-carbamimidoyl-benzyl)-3-[4-(1-oxy-pyridin-4-yl) benzoylamino]-butyric acid methyl ester or the pharmaceutically acceptable salt thereof is in the form of an infusion dose in the range from 0.10 mg/Kg body weight/h to 0.14 mg/Kg body weight/h.

* * * * *